(12) United States Patent
Bartholomew

(10) Patent No.: US 10,857,039 B2
(45) Date of Patent: Dec. 8, 2020

(54) HEMOSTATIC DEVICE

(71) Applicant: H. Chandler Bartholomew, Colorado Springs, CO (US)

(72) Inventor: H. Chandler Bartholomew, Colorado Springs, CO (US)

( * ) Notice: Subject to any disclaimer, the term of this patent is extended or adjusted under 35 U.S.C. 154(b) by 260 days.

(21) Appl. No.: 16/150,797

(22) Filed: Oct. 3, 2018

(65) Prior Publication Data

US 2020/0107969 A1    Apr. 9, 2020

(51) Int. Cl.
*A61F 13/20* (2006.01)
*A61F 13/26* (2006.01)
*A61F 13/00* (2006.01)
*A61F 13/36* (2006.01)
*A61B 17/00* (2006.01)
*A61B 17/12* (2006.01)
*B65D 81/32* (2006.01)

(52) U.S. Cl.
CPC ........ *A61F 13/2002* (2013.01); *A61F 13/266* (2013.01); *A61B 17/0057* (2013.01); *A61B 2017/12004* (2013.01); *A61F 13/00021* (2013.01); *A61F 13/36* (2013.01); *A61F 2013/00106* (2013.01); *A61L 2300/418* (2013.01); *A61L 2400/04* (2013.01); *B65D 81/32* (2013.01)

(58) Field of Classification Search
CPC ................ A61F 13/2002; A61F 13/266; A61F 13/00021; A61F 13/36; A61F 2013/00106; A61L 2400/04; A61L 2300/418; A61B 17/0057; A61B 2017/12004; B65D 81/32

USPC .......................................................... 604/15
See application file for complete search history.

(56) References Cited

U.S. PATENT DOCUMENTS

| 5,419,765 | A | 5/1995 | Weldon | |
|---|---|---|---|---|
| 6,261,258 | B1* | 7/2001 | Saines | A61B 17/0057 604/57 |
| D492,033 | S | 6/2004 | Jarmon | |
| 8,858,593 | B2* | 10/2014 | Kerber | A61B 17/0057 606/213 |
| 2007/0021703 | A1* | 1/2007 | McCarthy | A61L 26/0061 602/43 |
| 2008/0058691 | A1 | 3/2008 | Sorensen | |
| 2010/0158989 | A1* | 6/2010 | Mentkow | A61L 26/0066 424/447 |
| 2011/0077682 | A1* | 3/2011 | Gregory | A61L 15/425 606/213 |
| 2012/0179088 | A1 | 7/2012 | Ottuso | |
| 2013/0022552 | A1 | 1/2013 | Solomon | |

(Continued)

*Primary Examiner* — Andrew J Mensh

(57) ABSTRACT

A hemostatic device for treatment of a gunshot wound includes a barrel, which has a first end that is open, and a plunger. The barrel is arcuate adjacent to a second end to define a tip section. A clotting medium and a gauze are positioned in the barrel proximate to the tip section and between the clotting medium and the first end, respectively. A plurality of slits that is positioned in the tip section defines a plurality of petals, which comprise plastic and are resiliently deformable. The plunger, which has a head that is sealably positioned in the barrel adjacent to the first end, is configured to be pushed into the barrel to apply pressure to the gauze and the clotting medium so that the petals separate. The clotting medium and the gauze are sequentially expelled from the barrel into a wound to induce clotting and to pack the wound.

11 Claims, 3 Drawing Sheets

(56) References Cited

U.S. PATENT DOCUMENTS

| | | | |
|---|---|---|---|
| 2013/0190702 A1* | 7/2013 | Longo | F03B 13/1875 604/290 |
| 2013/0237898 A1* | 9/2013 | Kirkham | A61F 13/266 604/15 |
| 2014/0046239 A1* | 2/2014 | Taniguchi | A61F 13/266 604/11 |
| 2015/0289861 A1* | 10/2015 | MacPhee | A61L 27/26 604/311 |

* cited by examiner

HEMOSTATIC DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relate to hemostatic devices and more particularly pertains to a new hemostatic device for treatment of a gunshot wound.

BRIEF SUMMARY OF THE INVENTION

An embodiment of the disclosure meets the needs presented above by generally comprising a barrel, which has a first end that is open, and a plunger. The barrel is arcuate adjacent to a second end to define a tip section. A clotting medium and a gauze are positioned in the barrel proximate to the tip section and between the clotting medium and the first end, respectively. A plurality of slits that is positioned in the tip section defines a plurality of petals, which comprise plastic and are resiliently deformable. The plunger, which has a head that is sealably positioned in the barrel adjacent to the first end, is configured to be pushed into the barrel to apply pressure to the gauze and the clotting medium so that the petals separate. The clotting medium and the gauze are sequentially expelled from the barrel into a wound to induce clotting and to pack the wound.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
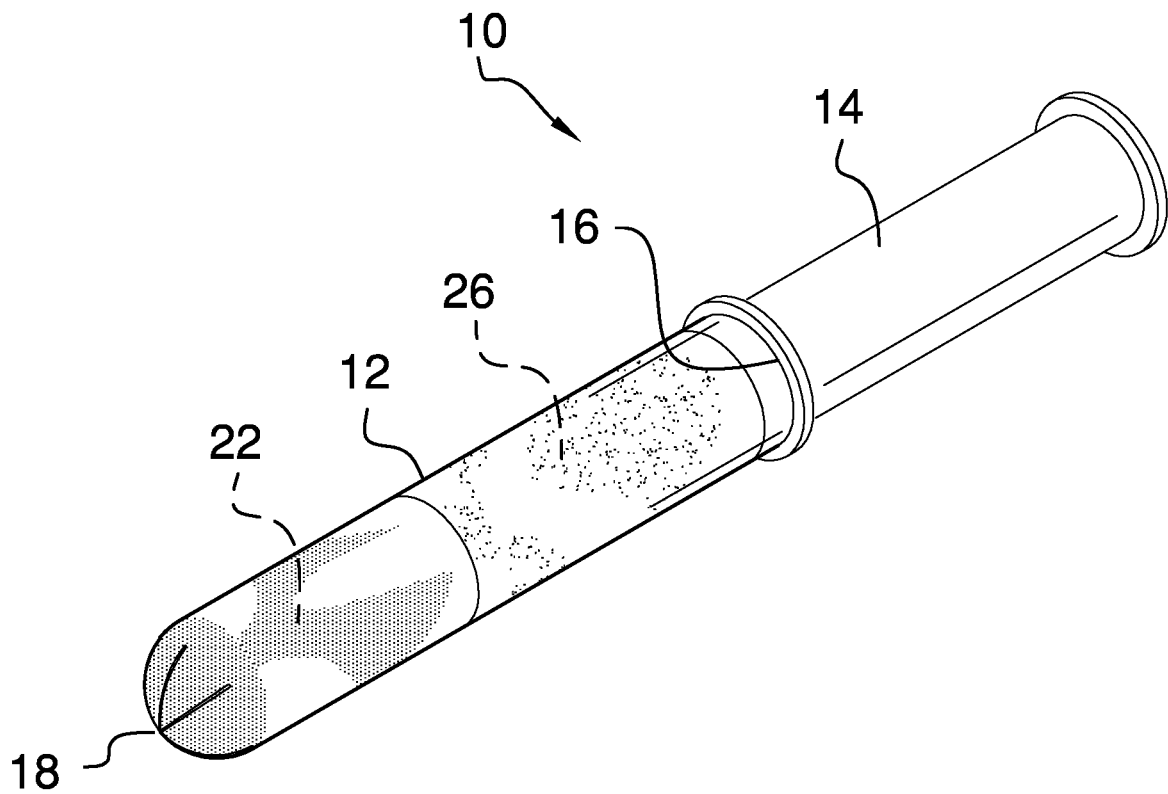
FIG. 1 is an isometric perspective view of a hemostatic device according to an embodiment of the disclosure.

With reference now to the drawings, and in particular to FIGS. 1 through 5 thereof, a new hemostatic device embodying the principles and concepts of an embodiment of the disclosure and generally designated by the reference numeral 10 will be described.

Figure 2:
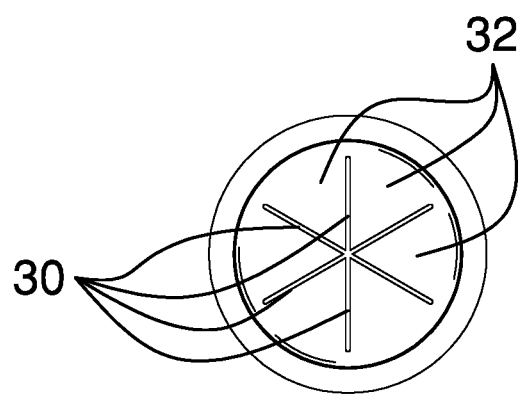
FIG. 2 is an end view of an embodiment of the disclosure.
Figure 3:
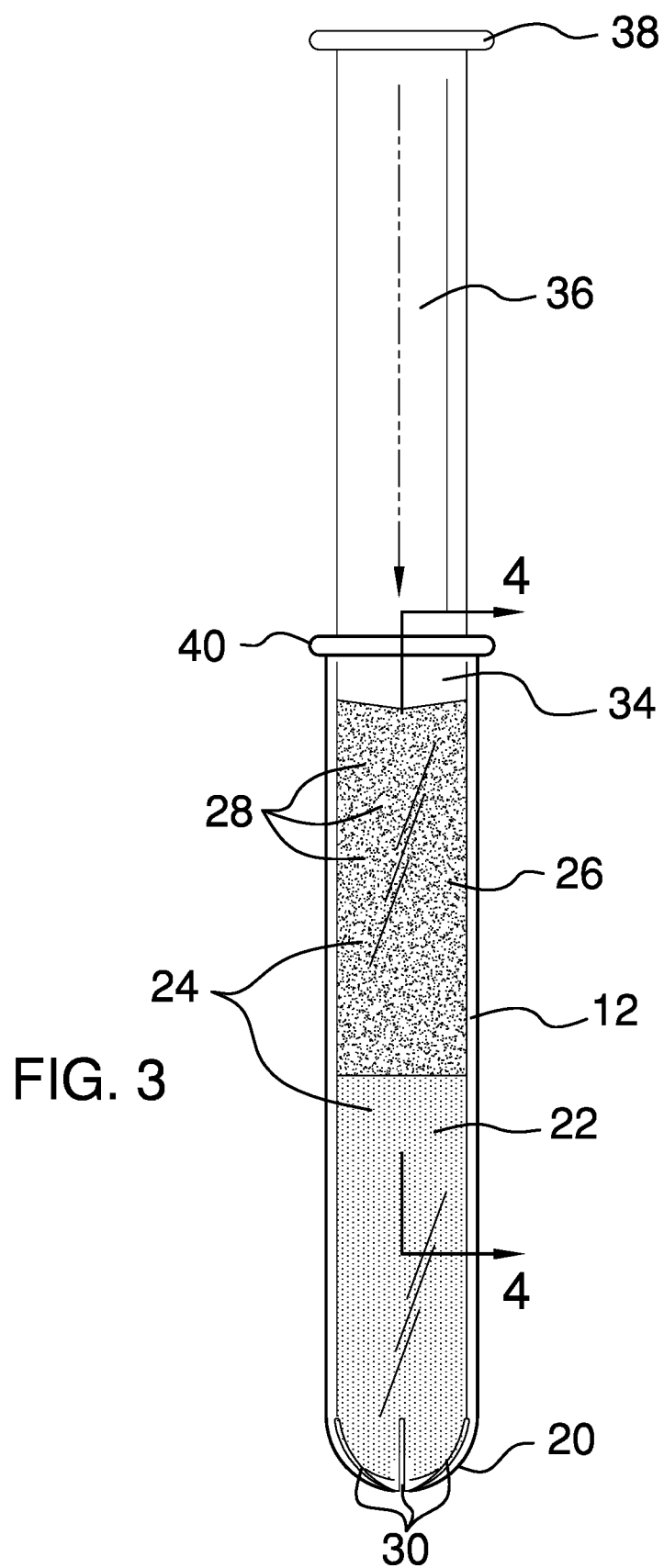
FIG. 3 is a side view of an embodiment of the disclosure.

As best illustrated in FIGS. 1 through 5, the hemostatic device 10 generally comprises a barrel 12 and a plunger 14. The barrel 12 has a first end 16 that is open. The barrel 12 is arcuate adjacent to a second end 18 to define a tip section 20 of the barrel 12, as shown in FIG. 3. The barrel 12 is circularly shaped between the tip section 20 and the first end 16. As will become apparent, the rounded shaped of the second end 18 and the circular shape of the barrel 12 facilitate insertion of the barrel 12 into a tract of a wound.

Figure 4:
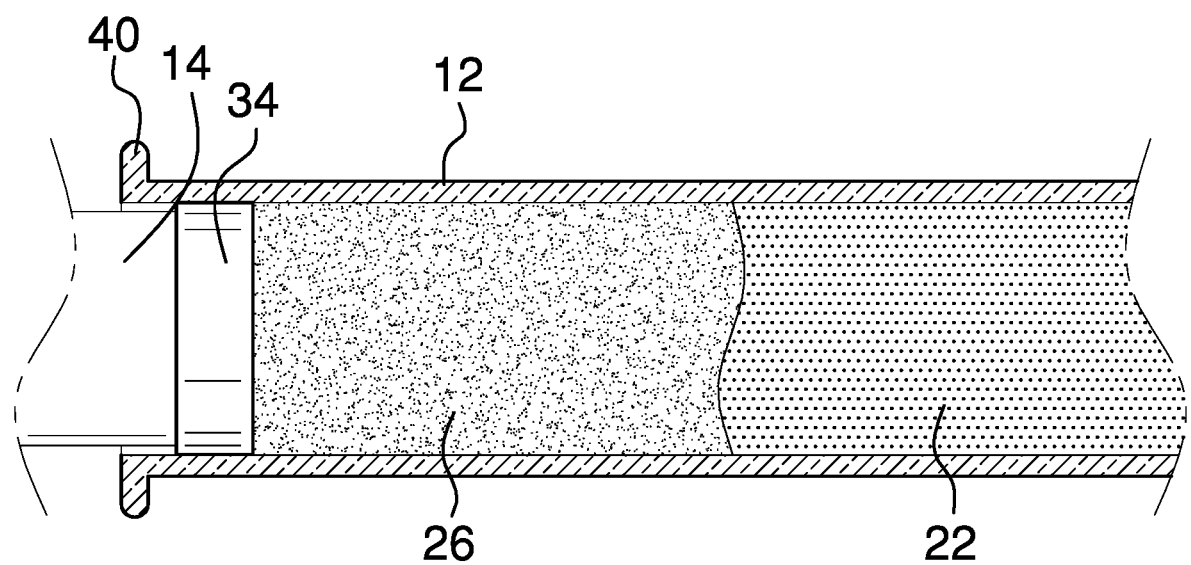
FIG. 4 is a cross-sectional view of an embodiment of the disclosure.
Figure 5:
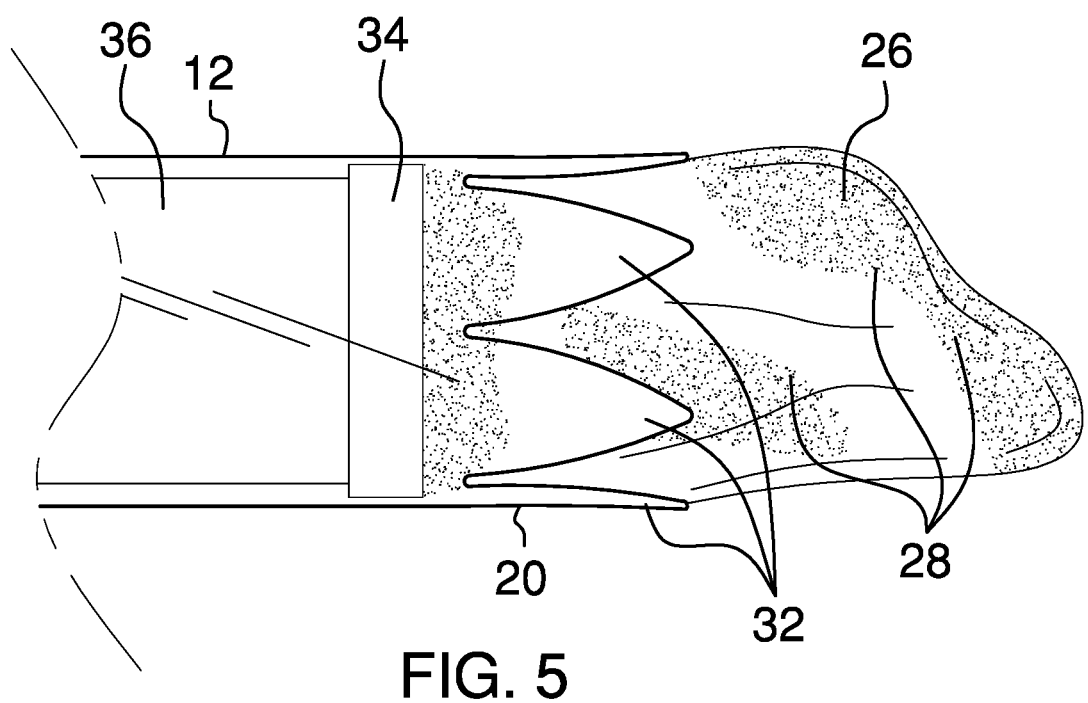
FIG. 5 is an in-use view of an embodiment of the disclosure.

A clotting medium 22 is positioned in the barrel 12 proximate to the tip section 20, as shown in FIG. 4. The clotting medium 22 comprises at least one of kaolin powder and pre-hydrated zeolite. The clotting medium 22 occupies substantially one half of a volume 24 of the barrel 12.

A gauze 26 is positioned in the barrel 12 between the clotting medium 22 and the first end 16, as shown in FIG. 4. The gauze 26 comprises at least one of rayon and cotton. The gauze 26 occupies substantially one half of the volume 24 of the barrel 12. The gauze 26 comprises a plurality of fibers 28. The fibers 28 are oriented so that the gauze 26 is configured to expand substantially radially.

A plurality of slits 30 is positioned in the tip section 20 to define a plurality of petals 32, as shown in FIG. 2. Each slit 30 extends from the second end 18 through the tip section 20. The petals 32 comprise plastic so that the petals 32 are resiliently deformable. The plurality of slits 30 comprises six slits 30. The petals 32 function to retain the clotting medium 22 and the gauze 26 in the barrel 12 prior to user. The petals 32 are designed to deform when pressure is applied to the clotting medium 22 and the gauze 26 so that they pivot relative to the barrel 12 to open the second end 18.

The plunger 14 has a head 34 that is sealably positioned in the barrel 12 adjacent to the first end 16. The head 34 functions to retain the clotting medium 22 and the gauze 26 in the barrel 12 prior to user. The plunger 14 is configured to be pushed into the barrel 12 to apply pressure to the gauze 26 and the clotting medium 22 so that the petals 32 separate.

The clotting medium 22 and the gauze 26 are sequentially expelled through the second end 18 of the barrel 12 into the wound, such as a gunshot wound, to induce clotting and to pack the wound. The clotting medium 22 induces platelet aggregation and clot formation, while the gauze 26 absorbs fluids within the wound. The absorption of the fluids induces the gauze 26 to swell, causing the gauze 26 to exert pressure along the tract of the wound so that bleeding is reduced or stopped. It is anticipated that the device 10 would be used to stabilize gunshot victims prior to or during transport to hospital, and that such use would reduce mortality due to gunshot wounds.

The plunger 14 and the barrel 12 comprise plastic. The plunger 14 comprises a shaft 36 that is coupled to and which extends between the head 34 and a flange 38. The shaft 36 is circumferentially smaller than the head 34, and the flange 38 is circumferentially larger than the shaft 36. A rim 40 is coupled to and extends radially from the first end 16 of the barrel 12. The rim 40 is configured to position digits of a hand of a user, positioning the user to urge the plunger 14 into the barrel 12 by pushing on the flange 38 with the thumb of the hand.

In use, the barrel 12 is inserted into tract of the wound and the plunger 14 is pushed through the barrel 12 to sequentially expel the clotting medium 22 and the gauze 26 through the second end 18 of the barrel 12 into the wound. The barrel 12 then is retracted from the wound. The clotting medium 22 induces clotting and the gauze 26 serves to pack the wound.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. A hemostatic device comprising:
   a barrel having a first end and a second end, the first end being open, the barrel being arcuate adjacent to the second end defining a tip section of the barrel;
   a clotting medium positioned in the barrel proximate to the tip section;
   a gauze positioned in the barrel between the clotting medium and the first end;
   a plurality of slits positioned in the tip section defining a plurality of petals, each slit extending from the second end through the tip section, the petals comprising plastic such that the petals are resiliently deformable; and
   a plunger having a head sealably positioned in the barrel adjacent to the first end wherein the plunger is configured for being pushed into the barrel for applying pressure to the gauze and the clotting medium such that the petals separate wherein the clotting medium and the gauze are sequentially expelled through the second end of the barrel into a wound for inducing clotting and packing the wound.

2. The device of claim 1, further including the barrel being circularly shaped between the tip section and the first end.

3. The device of claim 1, further including the barrel and the plunger comprising plastic.

4. The device of claim 1, further including the clotting medium comprising at least one of kaolin powder and pre-hydrated zeolite.

5. The device of claim 1, further including the gauze comprising at least one of rayon and cotton.

6. The device of claim 1, further comprising:
   the clotting medium occupying substantially one half of a volume of the barrel; and
   the gauze occupying substantially one half of the volume of the barrel.

7. The device of claim 1, further including the gauze comprising a plurality of fibers, the fibers being oriented such that the gauze is configured for expanding substantially radially.

8. The device of claim 1, further including the plurality of slits comprising six slits.

9. The device of claim 1, further including the plunger comprising a shaft coupled to and extending between the head and a flange, the shaft being circumferentially smaller than the head, the flange being circumferentially larger than the shaft.

10. The device of claim 1, further including a rim coupled to and extending radially from the first end of the barrel wherein the rim is configured for positioning digits of a hand of a user such that the user is positioned for urging the plunger into the barrel by pushing on the flange with the thumb of the hand.

11. A hemostatic device comprising:
    a barrel having a first end and a second end, the first end being open, the barrel being arcuate adjacent to the second end defining a tip section of the barrel, the barrel being circularly shaped between the tip section and the first end, the barrel comprising plastic;
    a clotting medium positioned in the barrel proximate to the tip section, the clotting medium comprising at least one of kaolin powder and pre-hydrated zeolite, the clotting medium occupying substantially one half of a volume of the barrel;
    a gauze positioned in the barrel between the clotting medium and the first end, the gauze comprising at least one of rayon and cotton, the gauze occupying substantially one half of the volume of the barrel, the gauze comprising a plurality of fibers, the fibers being oriented such that the gauze is configured for expanding substantially radially;
    a plurality of slits positioned in the tip section defining a plurality of petals, each slit extending from the second end through the tip section, the petals comprising plastic such that the petals are resiliently deformable, the plurality of slits comprising six slits;
    a plunger having a head sealably positioned in the barrel adjacent to the first end wherein the plunger is configured for being pushed into the barrel for applying pressure to the gauze and the clotting medium such that the petals separate wherein the clotting medium and the gauze are sequentially expelled through the second end of the barrel into a wound for inducing clotting and packing the wound, the plunger comprising plastic, the plunger comprising a shaft coupled to and extending between the head and a flange, the shaft being circumferentially smaller than the head, the flange being circumferentially larger than the shaft; and a rim coupled to and extending radially from the first end of the barrel wherein the rim is configured for positioning digits of a hand of a user such that the user is positioned for urging the plunger into the barrel by pushing on the flange with the thumb of the hand.

* * * * *